United States Patent
Gao et al.

(10) Patent No.: US 7,442,845 B2
(45) Date of Patent: Oct. 28, 2008

(54) CONVERSION OF ETHERS TO OLEFINS

(75) Inventors: Xiaoliang Gao, Calgary (CA); Andrzej Krzywicki, Calgary (CA); Stacy David Ross Johnston, Calgary (CA)

(73) Assignee: Nova Chemicals (International) S.A. (CH)

( * ) Notice: Subject to any disclaimer, the term of this patent is extended or adjusted under 35 U.S.C. 154(b) by 21 days.

(21) Appl. No.: 11/582,668

(22) Filed: Oct. 18, 2006

(65) Prior Publication Data

US 2007/0100186 A1    May 3, 2007

(30) Foreign Application Priority Data

Oct. 31, 2005   (CA) ..................................... 2524940

(51) Int. Cl.
*C07C 1/00*    (2006.01)
*B01J 23/00*   (2006.01)

(52) U.S. Cl. ........................ 585/640; 585/639; 502/355

(58) Field of Classification Search ................. 585/638, 585/640; 502/355
See application file for complete search history.

(56) References Cited

U.S. PATENT DOCUMENTS

2003/0065233 A1*   4/2003   Fuji et al. .................... 585/639

FOREIGN PATENT DOCUMENTS

DE            39 15 493 C2      5/1989
WO       WO 2004/052809 A1      6/2004

OTHER PUBLICATIONS

J. Am. Chem. Society, "Dehydration of Alcohols over Alumina Modified by Ammonia", 82(9), pp. 2401-2402, 1960.*

* cited by examiner

*Primary Examiner*—Glenn Caldarola
*Assistant Examiner*—In Suk Bullock
(74) *Attorney, Agent, or Firm*—Kenneth H. Johnson

(57) ABSTRACT

Ethers are cracked to olefins using a gamma-alumina catalyst in the presence of ammonia. The use of ammonia improves the selectivity to linear alpha olefins in comparison to cracking reactions in the absence of ammonia. The use of ammonia is convenient in comparison to known processes which employ alumina which as been treated with an amine. A preferred process produces octene-1 from 1-methoxyoctane.

4 Claims, No Drawings

CONVERSION OF ETHERS TO OLEFINS

FIELD OF THE INVENTION

This invention relates to the synthesis of olefins from ethers in the presence of an alumina catalyst and ammonia.

BACKGROUND OF THE INVENTION

The manufacture of higher olefins from ethylene is a well known art. The resulting olefins are subsequently used to prepare a wide variety of products including detergents, synthetic lubricants, and high molecular weight polymers and copolymers. Ethylene is a comparatively expensive material, so the use of alternative feedstocks such as propylene, butene or butadiene has also been investigated.

For example, U.S. Pat. No. 4,356,333 (Yoshimura et al.) discloses the dimerization of butadiene in an aqueous sulfolane solution, using a palladium catalyst, to product n-octadienol. This normal alcohol is useful for the manufacture of various synthetic resin modifiers and chemicals. It may also be selectively hydrogenated to n-octanol (which is useful in the synthesis of di-n-octyl phthalate which, in turn, is used as a plasticizer). Finally, the n-octanol may be dehydrated to produce octene. Thus, the synthesis of octene from butadiene involves three steps—dimerization, selective hydrogenation and dehydration.

It will be appreciated by those skilled in the art that each of the above described steps in the synthesis of octene from butadiene needs to be executed in an efficient manner in order to optimize the production of octene.

Similar processes have been reported in the patent literature. For example, U.S. Pat. No. 4,234,752 (Wiu et al.) disclosed the dehydration of alcohols in the presence of gamma-alumina. The gamma-alumina is preferably treated with a base.

Similarly, the abstract of German Patent 3,915,493 (assigned to Metallgesellschaft AG of Germany and Godrej Soaps Ltd. of India), discloses the synthesis of olefins from fatty alcohols in the presence of alumina which has been treated with ammonia.

World Patent application WO 2004/052809 (assigned to Oxeno) teaches the preparation of olefins from ethers using an alumina (with alkali or alkaline earth metal oxide) catalyst.

Finally, U.S. Patent application 2003/0065233 (assigned to Kuraray) discloses the synthesis of olefins from ethers or alcohols using alumina which has been treated with an organic amine.

However, the prior art does not disclose the conversion of ethers to olefins in the presence of ammonia. We have now discovered that olefins may be very efficiently produced from ethers using an alumina catalyst which has been treated with ammonia.

SUMMARY OF THE INVENTION

The present invention provides a process for the conversion of at least one ether to an olefin using a gamma-alumina catalyst, characterized in that process is conducted in the presence of ammonia.

In a preferred embodiment, octene-1 is selectively produced from 1-methoxyoctane using a gamma alumina catalyst which has been treated with ammonia.

DETAILED DESCRIPTION

This invention generally relates to the production of olefins. More specifically, it relates to the preparation of olefins from ethers. Thus, the invention provides a process to "split" or "crack" an ether to provide an olefin.

The process of this invention generally comprises reacting the ether with gamma-alumina. We have discovered that the use of ammonia in the cracking reaction improves the efficiency of the process to crack the ether to the olefin. While not wishing to be bound by theory, it is believed that the ammonia may partially neutralize some of the acidic sites on the gamma-alumina (or, alternatively, simply reduce the overall acidity of the gamma-alumina). The gamma-alumina still is highly active for the cracking reaction in the presence of ammonia, but an improved yield of the desired alpha-olefin is obtained in comparison to reactions which are conducted in the absence of ammonia.

A further aspect of the invention relates to the preferred amount of ammonia required to provide a balance of (i) activity; and (ii) "selectivity to alpha olefins". Another aspect of the invention relates to preferred reaction conditions, especially temperature and pressure.

In general, the market for alpha-olefins is better than the market for branched or internal olefins. Accordingly, it is desirable to maximize the yield of 1-olefins and minimize (i) double bond isomerization i.e. to minimize the formation of internal olefins); and (ii) skeletal isomerization (i.e. to minimize the formation of "branched" olefins).

Ethers which are "cracked" to olefins in accordance with this invention contain from about 4 to about 20 carbon atoms. The ethers may be straight chain or branched. It is highly preferred that the ether is a 1-methoxy ether—i.e. that the functional ether group is "—$OCH_3$".

Thus, the ethers which are preferably employed in the process of this invention may be illustrated by the following general formula:

R—$OCH_3$  formula I where R is a hydrocarbyl group having from about 3 to about 19 carbon atoms. It is preferred that the hydrocarbyl group R of the above formula is a saturated hydrocarbyl, especially a simple linear alkane. In general, the process of this invention uses "at least one" ether as a feedstock (i.e. a mixture of ethers may be used). However, it is preferred that the feed consists of substantially one ether. Thus, the preferred process of this invention might be generally described as the cracking or splitting of a 1-methoxy alkane to form an olefin.

It is especially preferred that the hydrocarbyl group R is a linear alkane containing from 6 to 10 carbon atoms, especially the following three ethers:

$CH_3O$—$C_6H_{13}$ $CH_3O$—$C_8H_{17}$ $CH_3O$—$C_{10}H_{21}$

The olefins which are preferably produced by the process of this invention correspond to the alpha olefin from which CH3OR has been removed from the ether. Thus, the preferred alpha olefins (corresponding to the three linear ethers noted above) are hexene-1, octene-1 and decene-1.

As previously noted, the present invention is characterized by the use of ammonia. In the absence of ammonia, the selectivity to alpha olefins is reduced, resulting in the production of isomerized olefins. Most preferably, the ammonia is used by simply mixing it with the ether prior to the cracking reaction. This may be done, for example, by (i) adding ammonia gas (i.e. $NH_3$ gas) to the ether; or (ii) adding an aqueous solution of ammonia ($NH_4OH$) to the ether. For the preferred ethers, especially those in which the group R of formula I is a saturated linear alkane containing from 6 to 10 carbon atoms, the "ammonia treatment" may be conventionally conducted at room temperature. It is preferred to have at least 25 parts per million by weight (ppm) ammonia based on the weight of the ether, with amounts of from 50 to 3,000 (especially 50 to 250) being especially preferred. The ammonia is preferably added to the ether prior to introducing the ether into the cracking reactor. In this manner, it is possible to add larger amounts of ammonia and the total amount of ammonia is preferably less than the solubility/saturation point of the ammonia in the ether. As an alternative, two separate feeds (of (1) the ether(s); and (2) the ammonia) may be sent to the "cracking" reactor.

The process of the present invention is preferably conducted in the substantial absence of any solvent or diluent for the ether. However, the scope of the present invention does not preclude the use of a solvent or diluent.

The cracking reaction is conducted in the presence of gamma-alumina. As used herein, the term "gamma-alumina" is meant to convey its conventional meaning, namely an alumina that is predominately in the gamma crystal form as determined by x-ray crystallography. Gamma-alumina is in commercial use as a catalyst (or catalyst support) and it is a widely available item of commerce. The use of a commercially available gamma-alumina is preferred. Such gamma-aluminas may be purchased in different forms (e.g. particulates or extrudates); particle sizes, surface areas, and pore sizes and pore volumes. The choice of the most preferred type of gamma-alumina will be influenced by conventional design considerations, including the cost of the commercially available gamma-alumina products and the configuration of the cracking reactor.

Two examples of commercially available gamma alumina which may be used in the process of this invention are sold under the trademark PURALOX KR® by Sasol and the tradename Al-4126E by Engelhard.

PURALOX KR® alumina is reported to have a surface area of 300 $m^2/g$ and a pore volume of 1 ml/g whereas Al-4126E alumina is reported to have a surface area of 235 $m^2/g$ and a pore volume of 0.8 cubic centimeters per gram.

The ether is thermally cracked in a reactor. The most preferred temperatures, pressures and reaction times may be readily determined by routine experimentation. In general, a temperature range of from about 150° C. to 500° C. is suitable (preferably, from about 275° C. to 450° C.).

A pressure range of from about atmospheric pressure to 3,500 KPa is suitable (with a preferred range of from about 100 to 1,000 KPa).

The reaction may be conducted in a batch or continuous mode of operation. It is preferred to operate in a continuous mode with a space velocity of from about 0.1 to 20 reciprocal hours ($h^{-1}$) WHSV, particularly from about 0.3 to 15 $h^{-1}$ and more particularly from about 8 to 12 $h^{-1}$. The term WHSV as used herein is meant to convey its conventional meaning, namely weight hourly space velocity (expressed as reciprocal hours) and is obtained by dividing the mass flow rate of the ether by the mass of the catalyst (gamma-alumina) in the reaction.

The present invention provides a high selectivity to alpha-olefin products. However, some by-products may be produced, and these by-products may be readily separated from the desired alpha-olefins using conventional separation techniques (e.g. solvent extraction or fractional distillation).

Further details are illustrated by the accompanying, non-limiting examples.

EXAMPLES

All "cracking" reactions were performed in a fixed bed tubular reactor. There are two separate heating zones in the system. The first zone, about 8" (about 20 cm) in length, is controlled at about 300° C. to vaporize the feed liquid and to maintain the vapor temperature close to the reaction temperature. The second zone contains a reactor having dimensions about 0.4" (about 1 cm) ID (internal diameter)× about 2" (about 5 cm) length. Both zones are controlled by independent thermocouples and temperature-control units. The ether (1-methoxyoctane) or "MOAN" was fed into the reactor at the top with a syringe pump. The product stream is passed through a condenser and the liquid is collected for analysis by gas chromatography (purchased from Agilent).

Comparative Example 1

Alumina extrudates (purchased from Engelhard under the tradename Al4126 E, in the form of 1/16" extrudates, then crushed to 20-40 mesh) were stirred in an aqueous solution of NaOH for five hours with a mechanical stirrer. The mixture was filtered to remove water and some fines. The solid was washed with water, dried at 135° C. overnight and then further dehydrated at 300° C. for five hours to form the base treated alumina catalyst. The catalyst was loaded into the reactor and was further stabilized at 300° C. overnight under nitrogen flow before a run started. 1-methoxyoctane was fed into the reactor for a half hour before a product sample was taken for analysis. For any change of the reaction conditions, such as change of WHSV or reaction temperature, the reaction was allowed to proceed for 0.5 hours before a sample was taken for analysis. The data from runs with NaOH-modified alumina are collected in Table 1.

Comparative Example 2

Alumina extrudates (Engelhard Al-4126 E crushed to 20-40 mesh) were dehydrated at 300° C. for five hours. A portion of the dehydrated alumina was loaded in the reactor and heated at 300° C. for 12 hours before a run started.

An amine was added to 1-methoxyoctane to form a 1 wt % solution of the amine in 1-methoxyoctane, which was fed into the reactor for the cracking runs. The experiments were performed in a similar manner to those in Comparative Example 1. The results are collected in Table 2.

Example 1

Ammonia gas was slowly bubbled through 1-methoxyoctane (50 mL) for 1 hour to form a saturated ammonia solution in 1-methoxyoctane. Analysis of ammonia in methoxyoctane indicated that the solution was saturated after 30 minutes of bubbling (15 min, 2372 mg $NH_3/L$; 30 min, 3016 mg $NH_3/L$; 60 min, 2924 mg $NH_3/L$; 90 min, 3294 mg $NH_3/L$). The $NH_3$ saturated methoxyoctane solution was used as feed to the cracking reactor. The data are presented in Table 3. ($NH_3$ helps to give higher conversion while maintaining high octene-1 selectivity.)

Example 2

An aqueous solution of $NH_4OH$ (0.8 mL, 28-30 wt %) was added to 1-methoxyoctane (50 mL) and the mixture was thoroughly mixed. The mixture was left to stand and only the organic layer was used for the cracking run. The experimental conditions were the same as in example 1 and the results are collected in Table 4.

Example 3

The conditions used in this Example were substantially the same as those of Example 1. Details are presented in Table 5.

Example 4

A second syringe pump was used to deliver ammonia from a gas-tight syringe into the feed stream. Table 6 and Table 7 show that when selectivity to 1-octene was high, conversion of MOAN can be tuned by varying the amount of ammonia delivered into the feed stream. Preferred operating conditions (high WHSV) and results (high octene-1 selectivity) may be achieved at low levels of ammonia, as shown in the Tables. Un-reacted MOAN and the produced n-octanol and dioctyl ether may be recycled to increase octene-1 yield. As shown in Table 8, octene-1 selectively was maintained at a very high level (>95%) at a WHSV between 8 and 12 using ammonia in an amount of from 50 to 250 ppm (based the weight of ammonia divided by the weight of MOAN).

TABLE 1

Cracking MOAN over NaOH Modified Alumina

| Run # | Catalyst | Sample | Temp (°C.) | WHSV ($h^{-1}$) | Flow (ml/hr) | MOAN Conversion (%) | Selectivity To Octenes (%) | 1-Octene Selectivity (%) | 1-Octene Yield (%) | Di-N-Octylether (%) |
|---|---|---|---|---|---|---|---|---|---|---|
| 1 | Al-4126 E 1/16" Extrudates (Engelhard) trial run | A | 300 | 3.5 | 7.7 | | | | | |
| | | B | 300 | 3.0 | 6.6 | | | | | |
| | | C | 300 | 4.0 | 8.8 | | | | | |
| 8 | Al-4126 E 1/16" Extrudates (Engelhard) + 1% Na2O | A | 280 | 3.0 | 7.3 | 11.30 | 39.62 | 98.78 | 39.14 | 48.14 |
| | | F | 300 | 4.0 | 9.7 | 12.36 | 38.65 | 98.71 | 38.15 | 42.20 |
| | | B | 300 | 3.0 | 7.3 | 17.96 | 39.91 | 98.90 | 39.48 | 42.29 |
| | | C | 300 | 2.0 | 4.9 | 23.37 | 41.86 | 98.94 | 41.42 | 38.16 |
| | smaller pieces of extrudates only, 1-3 mm | D | 300 | 1.0 | 2.4 | 35.42 | 49.41 | 98.89 | 48.86 | 25.81 |
| | | E | 300 | 0.5 | 1.2 | 50.96 | 64.06 | 98.45 | 63.06 | 39.28 |
| | | G | 320 | 3.0 | 7.3 | | | | 0.00 | #DIV/0! |
| 9 | Al-4126 E 1/16" Extrudates (Engelhard) + 0.5% Na2O 300 C. calcination | A | 280 | 3.0 | 7.2 | 25.96 | 56.22 | 98.78 | 55.53 | 28.06 |
| | | B | 300 | 3.0 | 7.2 | 36.72 | 64.46 | 98.43 | 63.44 | 22.30 |
| | | C | 300 | 2.0 | 4.8 | 39.02 | 70.37 | 98.41 | 69.25 | 17.03 |
| | | D | 300 | 1.0 | 2.4 | 59.24 | 79.15 | 97.82 | 77.43 | 11.87 |
| | | E | 300 | 0.5 | 1.2 | 78.72 | 88.56 | 96.14 | 85.14 | 5.40 |
| | smaller pieces of extrudates | F | 320 | 3.0 | 7.2 | 40.56 | 77.13 | 97.51 | 75.21 | 11.20 |
| 10 | Al-4126 E 1/16" Extrudates (Engelhard) + 0.25% Na2O | A | 300 | 3.0 | 7.2 | 90.35 | 95.67 | 84.24 | 80.59 | 0.52 |
| | | B | 300 | 2.0 | 4.8 | 94.09 | 96.06 | 79.54 | 76.40 | 0.25 |
| | | C | 300 | 1.0 | 2.4 | 92.55 | 96.15 | 64.46 | 61.98 | 0.42 |
| | | D | 300 | 0.5 | 1.2 | 98.34 | 96.63 | 45.32 | 43.80 | 0.22 |
| | smaller pieces of extrudates | E | 320 | 0.5 | 1.2 | 98.59 | 95.96 | 33.66 | 32.30 | 0.17 |
| 11 | Davicat Al 2750 spheres | A | 300 | 3.0 | 5.0 | 90.41 | 96.62 | 64.25 | 62.07 | 0.14 |
| | | B | 300 | 2.0 | 3.4 | 99.32 | 92.62 | 58.48 | 54.17 | 0.03 |
| | | C | 300 | 1.0 | 1.7 | 99.64 | 97.33 | 39.01 | 37.97 | 0.01 |
| | | D | 300 | 0.5 | 0.8 | 99.76 | 96.28 | 15.62 | 15.04 | 0.00 |
| | | E | 320 | 0.5 | 0.8 | 99.78 | 97.05 | 24.25 | 23.53 | 0.01 |
| 12 | Al-4126 E 1/16" Extrudates (Engelhard) + 0.5% Na2O 300 C. calcination | A | 300 | 3.0 | 7.2 | 65.95 | 82.50 | 98.11 | 80.94 | 8.77 |
| | | B | 300 | 2.0 | 4.8 | 75.22 | 87.77 | 97.70 | 85.76 | 5.49 |
| | | C | 300 | 1.0 | 2.4 | 94.02 | 95.78 | 95.06 | 91.05 | 0.57 |
| | | D | 300 | 0.5 | 1.2 | 97.33 | 97.44 | 87.43 | 85.19 | 0.25 |
| | 20-40 mesh | E | 320 | 0.5 | 1.2 | 98.72 | 88.69 | 79.48 | 70.50 | 0.06 |

TABLE 2

Cracking MOAN over Alumina in the Presence of Amines

| Run # | Catalyst | Sample | Temp (°C.) | WHSV ($h^{-1}$) | Flow (ml/hr) | MOAN Conversion (%) | Selectivity To Octenes (%) | 1-Octene Selectivity (%) | 1-Octene Yield (%) | Di-N-Octylether (%) |
|---|---|---|---|---|---|---|---|---|---|---|
| 1 | Al-4126 E 1/16" Extrudates (Engelhard) trial run | A | 300 | 3.5 | 7.7 | | | | | |
| | | B | 300 | 3.0 | 6.6 | | | | | |
| | | C | 300 | 4.0 | 8.8 | | | | | |
| 20 | Al-4126 E 1/16" Extrudates (Engelhard) - 300 C. calcination | A | 300 | 3.0 | 6.5 | 80.27 | 91.33 | 94.61 | 86.40 | 2.25 |
| | | B | 300 | 2.0 | 4.3 | 84.11 | 91.78 | 95.46 | 87.61 | 2.10 |
| | | C | 300 | 1.0 | 2.2 | 93.50 | 94.77 | 93.60 | 88.71 | 0.46 |
| | 1 wt % 2-Me2N-Pyridine dissolved in MOAN | D | 300 | 0.5 | 1.1 | 96.37 | 95.43 | 89.36 | 85.28 | 0.35 |
| | | E | 320 | 0.5 | 1.1 | 97.99 | 93.36 | 86.56 | 80.81 | 0.13 |
| 21 | Al-4126 E 1/16" Extrudates (Engelhard) - 300 C. calcination | A | 300 | 3.0 | 6.1 | 48.92 | 76.40 | 98.37 | 75.15 | 10.75 |
| | | B | 300 | 2.0 | 4.1 | 64.19 | 82.00 | 97.30 | 79.79 | 8.09 |
| | | C | 300 | 1.0 | 2.0 | 75.31 | 87.40 | 91.59 | 80.05 | 5.45 |
| | 1 wt % Me2N(CH2)6NMe2 dissolved in MOAN | D | 300 | 0.5 | 1.0 | 76.61 | 87.93 | 82.50 | 72.54 | 5.28 |
| | | E | 320 | 0.5 | 1.0 | 78.36 | 91.79 | 65.24 | 59.89 | 1.64 |

TABLE 3

Cracking MOAN over Alumina in the Presence of Ammonia

| Run # | Catalyst | Sample | Temp (° C.) | WHSV (h⁻¹) | Flow (ml/hr) | MOAN Conversion (%) | Selectivity To Octenes (%) | 1-Octene Selectivity (%) | 1-Octene Yield (%) | Di-N-Octylether (%) |
|---|---|---|---|---|---|---|---|---|---|---|
| 1 | Al-4126 E 1/16" Extrudates (Engelhard) trial run | A | 300 | 3.5 | 7.7 | | | | | |
| | | B | 300 | 3.0 | 6.6 | | | | | |
| | | C | 300 | 4.0 | 8.8 | | | | | |
| 30 | Al-4126 E 1/16" Extrudates | A | 300 | 3.0 | 8.3 | 81.91 | 77.40 | 97.42 | 75.40 | 2.46 |
| | | B | 300 | 2.0 | 5.5 | 93.17 | 91.10 | 96.67 | 88.07 | 0.44 |
| | NH3 bubbled through | C | 300 | 1.0 | 2.8 | 98.90 | 94.78 | 92.69 | 87.86 | 0.06 |
| | MOAN for 1 hr | D | 300 | 0.5 | 1.4 | 99.46 | 96.07 | 83.92 | 80.62 | 0.05 |
| | 20-40 mesh | F | 300 | 5.0 | 13.8 | 71.02 | 79.82 | 97.92 | 78.16 | 5.63 |

TABLE 4

Cracking MOAN over Alumina in the Presence of Ammonia/H2O

| Run # | Catalyst | Sample | Temp (° C.) | WHSV (h⁻¹) | Flow (ml/hr) | MOAN Conversion (%) | Selectivity to Octenes (%) | 1-Octene Selectivity (%) | 1-Octene Yield (%) | Di-N-Octylether (%) |
|---|---|---|---|---|---|---|---|---|---|---|
| 1 | Al-4126 E 1/16" Extrudates (Engelhard) trial run | A | 300 | 3.5 | 7.7 | | | | | |
| | | B | 300 | 3.0 | 6.6 | | | | | |
| | | C | 300 | 4.0 | 8.8 | | | | | |
| 32 | Al-4126 E 1/16" Extrudates | A | 300 | 3.0 | 8.1 | 99.03 | 94.47 | 92.17 | 87.07 | 0.02 |
| | | B | 300 | 2.0 | 5.4 | 99.77 | 96.07 | 87.81 | 84.36 | 0.01 |
| | NH4OH added to feed | C | 300 | 1.0 | 2.7 | 99.97 | 96.25 | 75.13 | 72.31 | 0.02 |
| | | D | 300 | 0.5 | 1.4 | 100.00 | 96.21 | 57.16 | 54.99 | 0.01 |
| | 20-40 mesh | E | 300 | 0.5 | 1.4 | 100.00 | 94.25 | 32.73 | 30.85 | 0.01 |

TABLE 5

Cracking MOAN over Alumina in the Presence of Ammonia

| Run # | Catalyst | Sample | Temp (° C.) | WHSV (h⁻¹) | Flow (ml/hr) | MOAN Conversion (%) | Selectivity To Octenes (%) | 1-Octene Selectivity (%) | 1-Octene Yield (%) | Di-N-Octylether (%) |
|---|---|---|---|---|---|---|---|---|---|---|
| 1 | Al-4126 E 1/16" Extrudates (Engelhard) trial run | A | 300 | 3.5 | 7.7 | | | | | |
| | | B | 300 | 3.0 | 6.6 | | | | | |
| | | C | 300 | 4.0 | 8.8 | | | | | |
| 38 | Al-4126 E 1/16" Extrudates 20-40 mesh | A | 300 | 2.0 | 4.4 | 90.88 | 92.04 | 96.78 | 89.08 | 0.88 |
| | | B | 300 | 1.0 | 2.2 | 98.50 | 95.31 | 93.31 | 88.93 | 0.06 |
| | NH3 bubbled through | C | 300 | 0.5 | 1.1 | 99.90 | 96.65 | 85.77 | 82.90 | 0.00 |
| | MOAN for 1 hr | D N2 gas 50 cc/min | 300 | 0.5 | 1.1 | 99.44 | 96.52 | 94.41 | 91.12 | 0.06 |
| | | E N2 gas 175 cc/min | 300 | 0.5 | 1.1 | 99.58 | 97.53 | 95.72 | 93.36 | 0.06 |

TABLE 6

Cracking MOAN over Alumina in the Presence of Different Amounts of Ammonia

| Run # | NH3 (ml/hr) | NH3 (ppm) | Sample | Temp (° C.) | WHSV (h⁻¹) | Flow Rate (ml/hr) | C (%) | S_{C8s} (%) | S_{C8-1} (%) | (n-Octyl)2O (%) | n-Octyl-OH | MeOH | MeOMe |
|---|---|---|---|---|---|---|---|---|---|---|---|---|---|
| 1 | | | A | 300 | 3.5 | 7.7 | | | | | | | |
| | | | B | 300 | 3.0 | 6.6 | | | | | | | |
| | | | C | 300 | 4.0 | 8.8 | | | | | | | |
| 68 | 20 | 703 | A | 300 | 9.8 | 20 | 54.96 | 73.96 | 98.34 | 10.62 | 7.66 | 0.96 | 3.12 |
| | 20 | 703 | B | 300 | 9.8 | 20 | 53.06 | 76.95 | 98.33 | 10.20 | 7.49 | 0.60 | 1.18 |
| | 8.7 | 250 | C | 300 | 12.0 | 24.4 | 74.66 | 88.02 | 97.46 | 2.31 | 4.03 | 0.56 | 1.99 |
| | 8.7 | 500 | D | 300 | 6.0 | 12.2 | 77.34 | 90.29 | 97.34 | 2.39 | 3.68 | 0.21 | 0.41 |
| | 8.7 | 750 | E | 300 | 4.0 | 8.2 | 83.66 | 88.20 | 96.94 | 1.55 | 2.79 | 0.40 | 3.77 |
| | 8.7 | 1500 | F | 300 | 2.0 | 4.1 | 87.62 | 90.83 | 96.26 | 0.94 | 1.99 | 0.31 | 2.10 |

Catalyst: Engelhard Al-4126 E 1/16" extrudates, calcined at 300° C., 20-40 mesh

TABLE 7

Cracking MOAN over Alumina in the Presence of Different Amounts of Ammonia

| Run # | NH3 (ml/hr) | NH3 (ppm) | Sample | Temp (° C.) | WHSV (h⁻¹) | Flow Rate (ml/hr) | C (%) | $S_{C8s}$ (%) | $S_{C8-1}$ (%) | (n-Octyl)₂O (%) | n-Octyl-OH | MeOH | MeOMe |
|---|---|---|---|---|---|---|---|---|---|---|---|---|---|
| 1 |  |  | A | 300 | 3.5 | 7.7 |  |  |  |  |  |  |  |
|  |  |  | B | 300 | 3.0 | 6.6 |  |  |  |  |  |  |  |
|  |  |  | C | 300 | 4.0 | 8.8 |  |  |  |  |  |  |  |
| 70 | 0 | 0 | A | 300 | 4.0 | 7.5 | 100.00 | 95.69 | 65.39 | 0.01 | 0.01 | 0.10 | 1.55 |
|  | 21.4 | 2140 | B | 300 | 4.0 | 7.5 | 55.21 | 67.41 | 97.59 | 14.37 | 8.23 | 0.82 | 3.14 |
|  | 16.1 | 1610 | C | 300 | 4.0 | 7.5 | 62.39 | 76.12 | 98.24 | 8.80 | 6.82 | 0.69 | 2.58 |
|  | 10.7 | 1070 | D | 300 | 4.0 | 7.5 | 84.99 | 91.81 | 93.95 | 0.80 | 2.18 | 0.38 | 2.65 |
|  | 5.4 | 540 | E | 300 | 4.0 | 7.5 | 83.75 | 90.24 | 96.92 | 1.38 | 2.77 | 0.36 | 2.11 |
|  | 1.1 | 100 | F | 300 | 4.0 | 7.5 | 91.87 | 93.66 | 95.61 | 0.4 | 1.44 | 0.20 | 1.43 |
| 73 | 1.1 | 100 | B | 300 | 4.0 | 7.5 | 97.13 | 94.78 | 93.73 | 0.06 | 0.53 | 0.14 | 1.85 |
|  | 1.6 | 100 | C | 300 | 6.0 | 11.3 | 92.65 | 93.39 | 95.31 | 0.35 | 1.30 | 0.22 | 2.18 |
|  | 2.2 | 100 | D | 300 | 8.0 | 15.1 | 89.77 | 92.36 | 95.80 | 0.54 | 1.70 | 0.31 | 2.60 |
|  | 2.7 | 100 | E | 300 | 10.0 | 18.8 | 87.38 | 92.13 | 96.01 | 0.69 | 2.03 | 0.34 | 2.22 |

Catalyst: Sasol PURALOX KR extrudates, calcined at 300° C., 20-40 mesh

TABLE 8

Cracking MOAN over Alumina in the Presence of Different Amounts of Ammonia

| Run # | NH3 (ml/hr) | NH3 (ppm) | Sample | Temp (° C.) | WHSV (h⁻¹) | Flow Rate (ml/hr) | C (%) | $S_{C8s}$ (%) | $S_{C8-1}$ (%) | (n-Octyl)₂O (%) | n-Octyl-OH | MeOH | MeOMe |
|---|---|---|---|---|---|---|---|---|---|---|---|---|---|
| 76 | 0.0 | 0 | A | 300 | 8.0 | 13.1 | 99.50 | 96.82 | 88.88 | 0.01 | 0.08 | 0.18 | 3.05 |
|  | 1.9 | 100 | B | 300 | 8.0 | 13.1 | 88.22 | 95.47 | 95.25 | 0.40 | 1.59 | 0.26 | 1.84 |
|  | 4.7 | 250 | C | 300 | 8.0 | 13.1 | 78.30 | 92.16 | 97.06 | 1.70 | 3.35 | 0.57 | 4.66 |
|  | 9.7 | 500 | D | 300 | 8.0 | 13.1 | 62.00 | 84.14 | 98.22 | 5.74 | 6.22 | 0.88 | 4.39 |
|  | 18.7 | 1000 | E | 300 | 8.0 | 13.1 | 43.90 | 69.76 | 98.87 | 13.79 | 9.67 | 1.11 | 4.25 |
|  | 28.1 | 1500 | F | 300 | 8.0 | 13.1 | 39.24 | 65.52 | 98.95 | 15.50 | 10.62 | 1.20 | 3.91 |
| 77 | 0.0 | 0 | A | 300 | 10.0 | 16.4 | 95.18 | 96.63 | 94.73 | 0.08 | 0.80 | 0.12 | 1.53 |
|  | 1.2 | 50 | B | 300 | 10.0 | 16.4 | 85.86 | 94.63 | 96.43 | 0.66 | 2.23 | 0.33 | 1.61 |
|  | 2.3 | 100 | C | 300 | 10.0 | 16.4 | 79.90 | 92.78 | 96.97 | 1.41 | 3.28 | 0.39 | 1.31 |
|  | 3.5 | 150 | D | 300 | 10.0 | 16.4 | 78.59 | 92.61 | 97.04 | 1.48 | 3.30 | 0.51 | 2.02 |
|  | 4.7 | 200 | E | 300 | 10.0 | 16.4 | 72.15 | 90.16 | 97.63 | 2.59 | 4.46 | 0.54 | 1.92 |
|  | 5.6 | 200 | F | 300 | 12.0 | 19.6 | 72.27 | 90.54 | 97.61 | 2.32 | 4.39 | 0.56 | 1.47 |
|  | 4.2 | 150 | G | 300 | 12.0 | 19.6 | 75.33 | 91.66 | 97.45 | 1.78 | 3.88 | 0.47 | 1.34 |
|  | 2.8 | 100 | H | 300 | 12.0 | 19.6 | 80.12 | 92.88 | 97.22 | 1.22 | 3.17 | 0.62 | 4.55 |

Catalyst: Sasol PURALOX KR extrudates, calcined at 300° C., 20-40 mesh

What is claimed is:

1. A process for the conversion of 1-methoxyoctane to octene-1 using a gamma alumina catalyst, characterized in that process is conducted in the presence of ammonia.

2. The process of claim 1 when completed at a temperature of from 150° C. to 500° C. and a pressure of from atmospheric pressure to 3,500 KPa.

3. The process of claim 1 when conducted in a continuous mode of operation at a WHSV space velocity of from 0.1 to 20 h⁻¹.

4. The process of claim 1 when conducted at a WHSV of from 8 to 12 h⁻¹ and ammonia concentration of from 50 to 250 ppm, based on the weight of said at least one ether.

* * * * *